United States Patent
Liversidge

(10) Patent No.: US 7,828,778 B2
(45) Date of Patent: Nov. 9, 2010

(54) MEDICAL INJECTOR HANDLING DEVICE

(75) Inventor: Barry Peter Liversidge, The Wick, Wick Road, Langham, Colchester, Essex (GB) C04 5PE

(73) Assignee: Barry Peter Liversidge, Colchester, Essex (GB)

( * ) Notice: Subject to any disclaimer, the term of this patent is extended or adjusted under 35 U.S.C. 154(b) by 544 days.

(21) Appl. No.: 10/589,122

(22) PCT Filed: Feb. 11, 2005

(86) PCT No.: PCT/GB2005/000487
§ 371 (c)(1),
(2), (4) Date: Aug. 10, 2006

(87) PCT Pub. No.: WO2005/079889
PCT Pub. Date: Sep. 1, 2005

(65) Prior Publication Data
US 2007/0173772 A1    Jul. 26, 2007

(30) Foreign Application Priority Data
Feb. 14, 2004    (GB) .................................. 0403335.3

(51) Int. Cl.
*A61M 5/32*    (2006.01)
(52) U.S. Cl. ................... 604/198; 604/111; 604/181; 604/187; 604/192; 604/263; 128/919
(58) Field of Classification Search .............. 604/192, 604/187, 181, 198, 263, 110, 188, 197, 500, 604/506, 93.01, 111, 48, 513; 128/919, 917
See application file for complete search history.

(56) References Cited

U.S. PATENT DOCUMENTS 4,702,737 A * 10/1987 Pizzino ..................... 604/191
4,772,272 A *  9/1988 McFarland ................ 604/198

(Continued)

FOREIGN PATENT DOCUMENTS

EP          0409180         1/1991

(Continued)

*Primary Examiner*—Kevin C. Sirmons
*Assistant Examiner*—Shefali D Patel
(74) *Attorney, Agent, or Firm*—Andrus, Sceales, Starke & Sawall, LLP

(57) ABSTRACT

A handling device for use with a medical injector (11) including a protective sheath (17) for a needle (14) has a carrier (20) with an outer cylindrical wall (21) and a coaxial inner tube (33) which is a close sliding fit over the protective sheath (17). A cylindrical sleeve (24) is slidably mounted within the outer cylindrical wall (21) and is adapted to receive the cylindrical body (12) of the injector (11). A bushing (25) is slidably retained within the cylindrical sleeve (24) and is configured to receive a boss (13, 15) supporting the needle (14) at the forward end of the injector body, a spring (29) urging the bushing (25) towards the rear of the sleeve. A plug (35) is mounted on the carrier (20) and is engaged by the forward end of the protective sheath (17) when the injector is received within the cylindrical sleeve, so that the plug is projected forwardly from the carrier when the injector is fully engaged. On removing the carrier (20) from the injector (11), the plug (35) remains projecting therefrom and the sheath (17) is removed together with the carrier.

20 Claims, 6 Drawing Sheets

U.S. PATENT DOCUMENTS

| | | | |
|---|---|---|---|
| 4,955,865 A * | 9/1990 | Steiner et al. | 604/192 |
| 4,976,701 A * | 12/1990 | Ejlersen et al. | 604/192 |
| 5,067,949 A * | 11/1991 | Freundlich et al. | 604/263 |
| 5,137,516 A * | 8/1992 | Rand et al. | 604/136 |
| 5,436,994 A * | 7/1995 | Ott et al. | 385/86 |
| 5,928,205 A * | 7/1999 | Marshall | 604/263 |
| 6,776,777 B2 * | 8/2004 | Barrelle | 604/198 |
| 2005/0171484 A1 * | 8/2005 | Jangula | 604/198 |
| 2006/0100588 A1 * | 5/2006 | Brunnberg et al. | 604/192 |
| 2006/0173408 A1 * | 8/2006 | Wyrick | 604/110 |

FOREIGN PATENT DOCUMENTS

| | | | |
|---|---|---|---|
| EP | 409180 A1 * | 1/1991 | |
| WO | WO 8802638 | 4/1988 | |

* cited by examiner

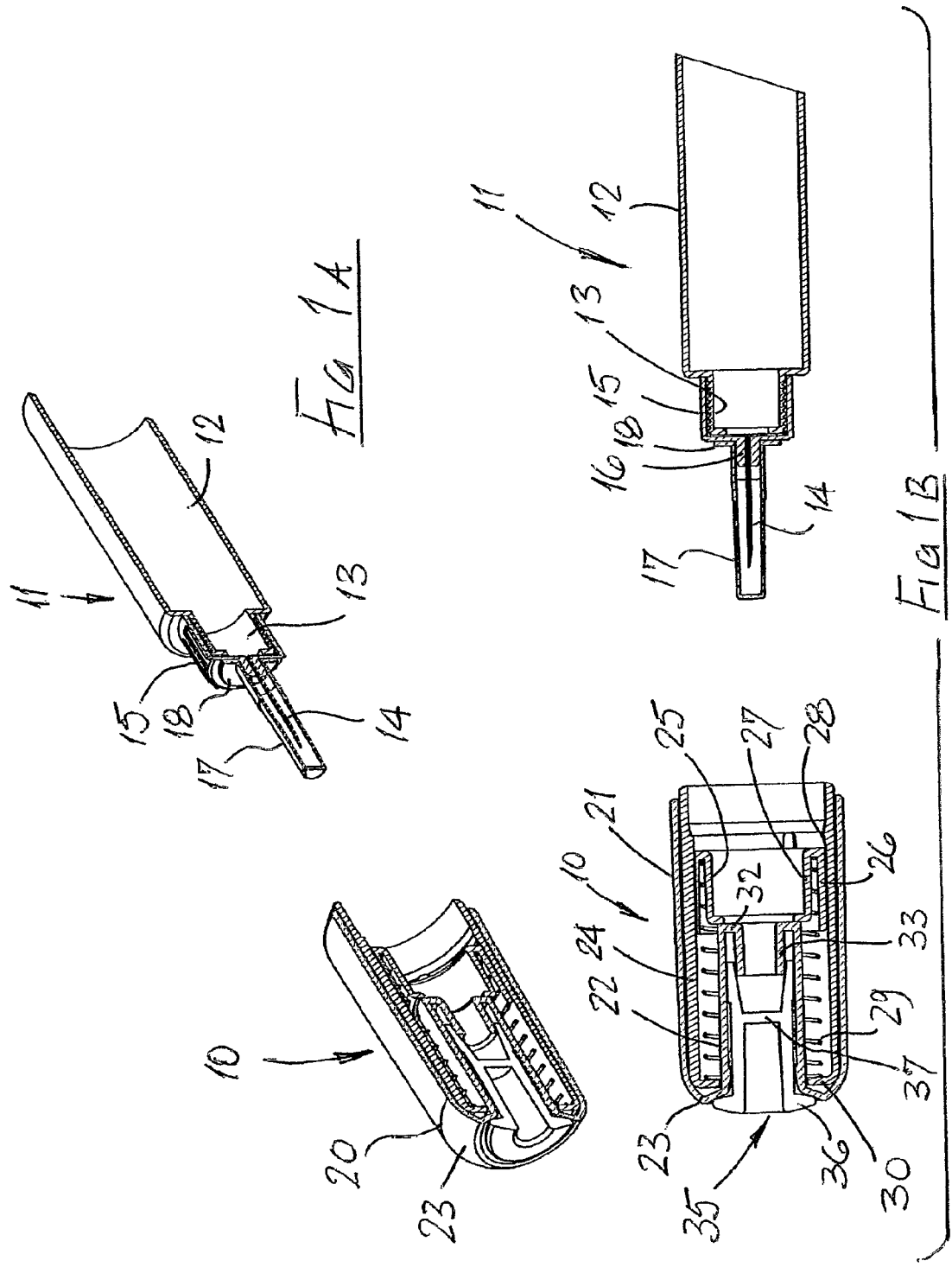

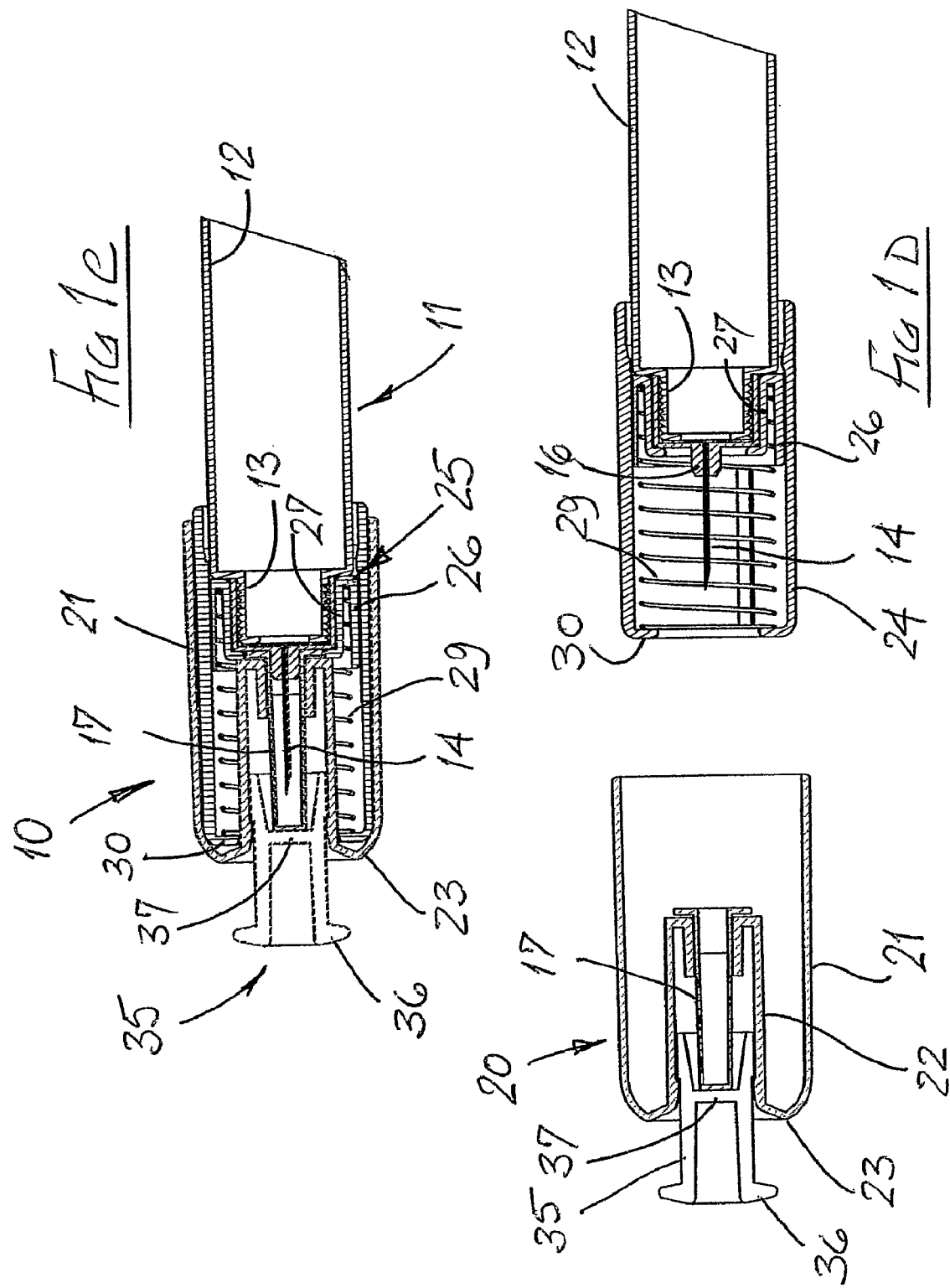

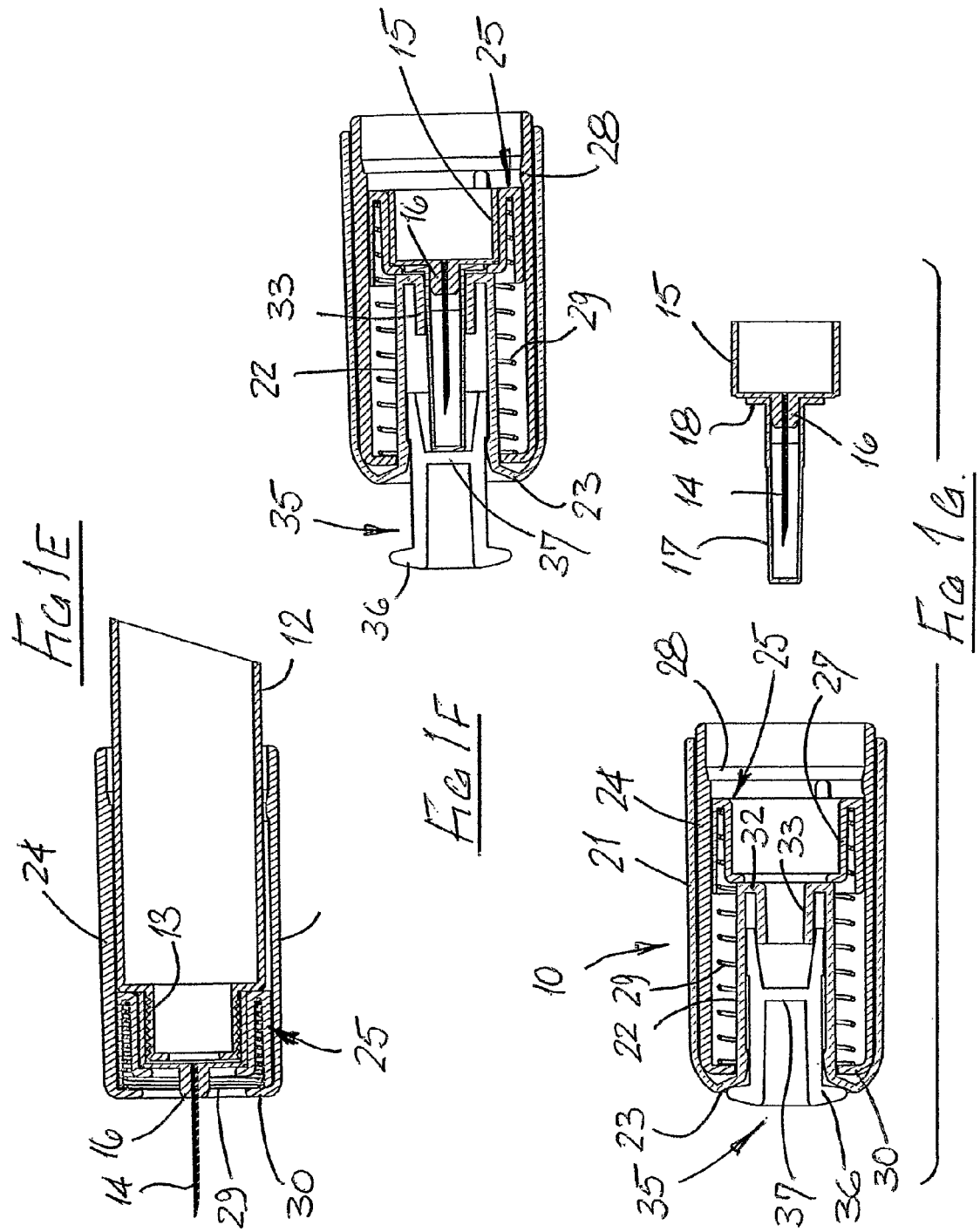

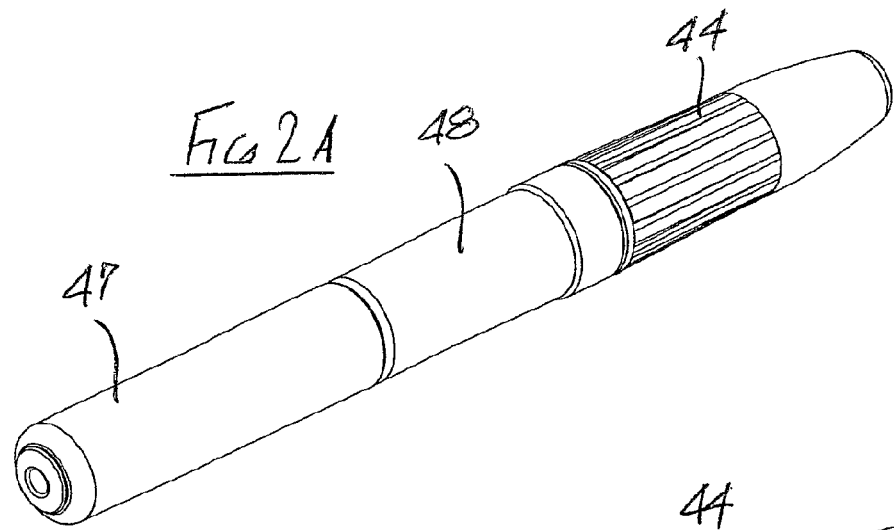
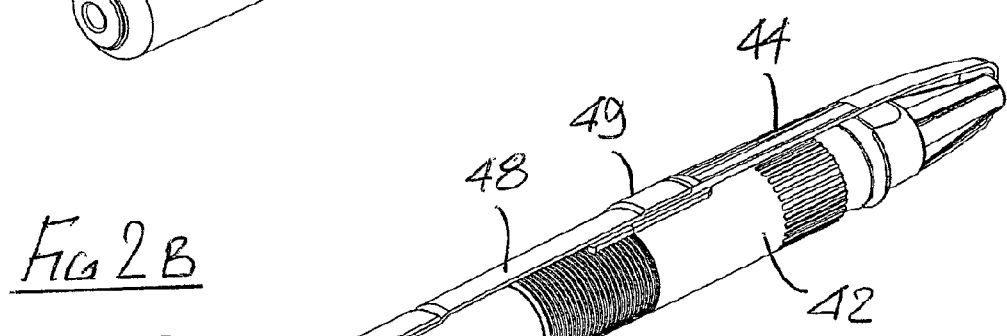
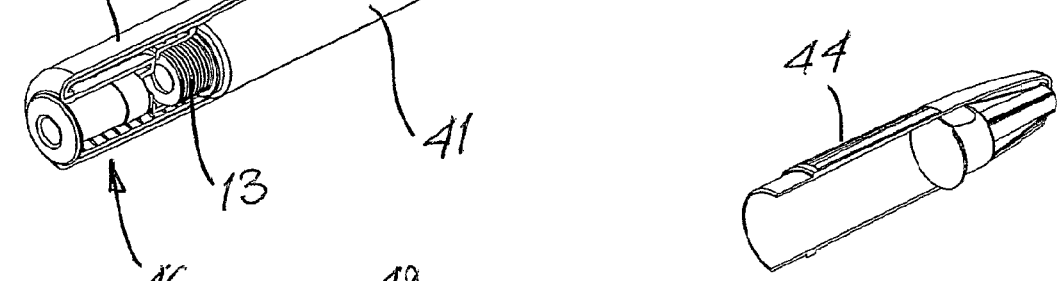
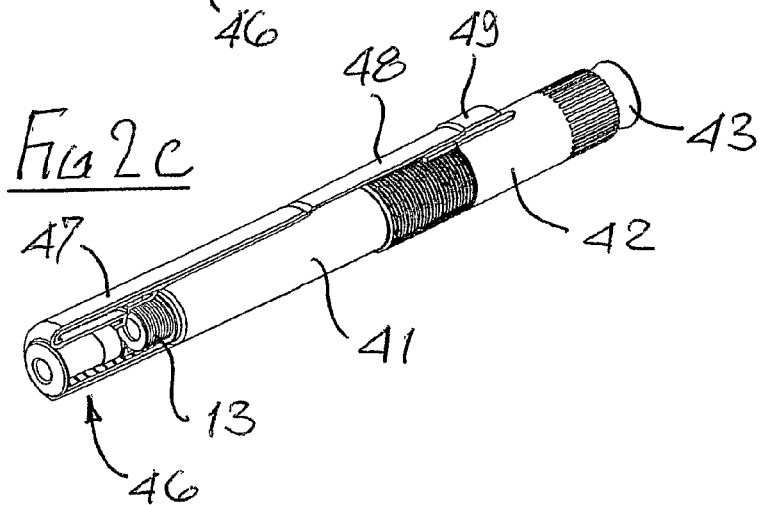

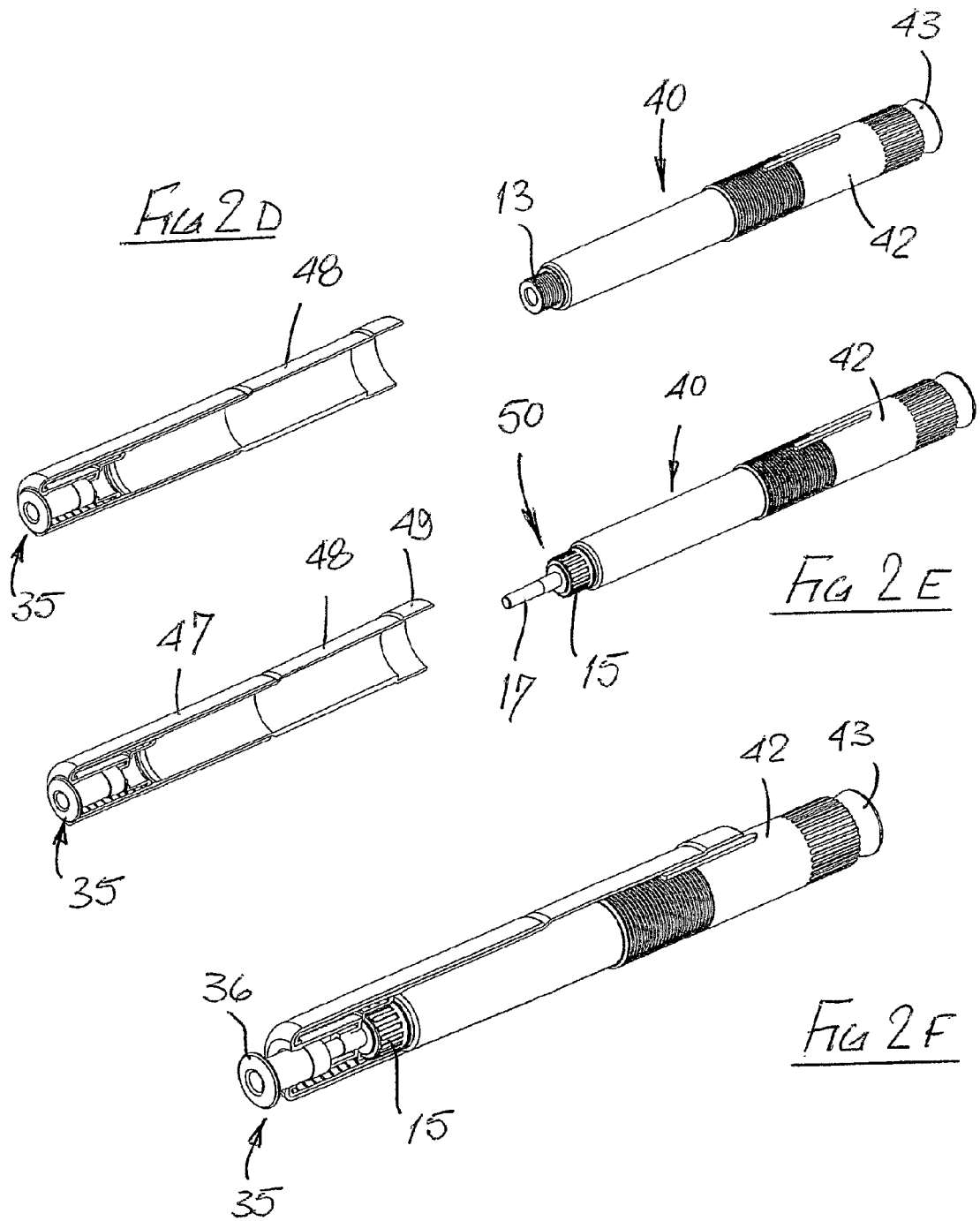

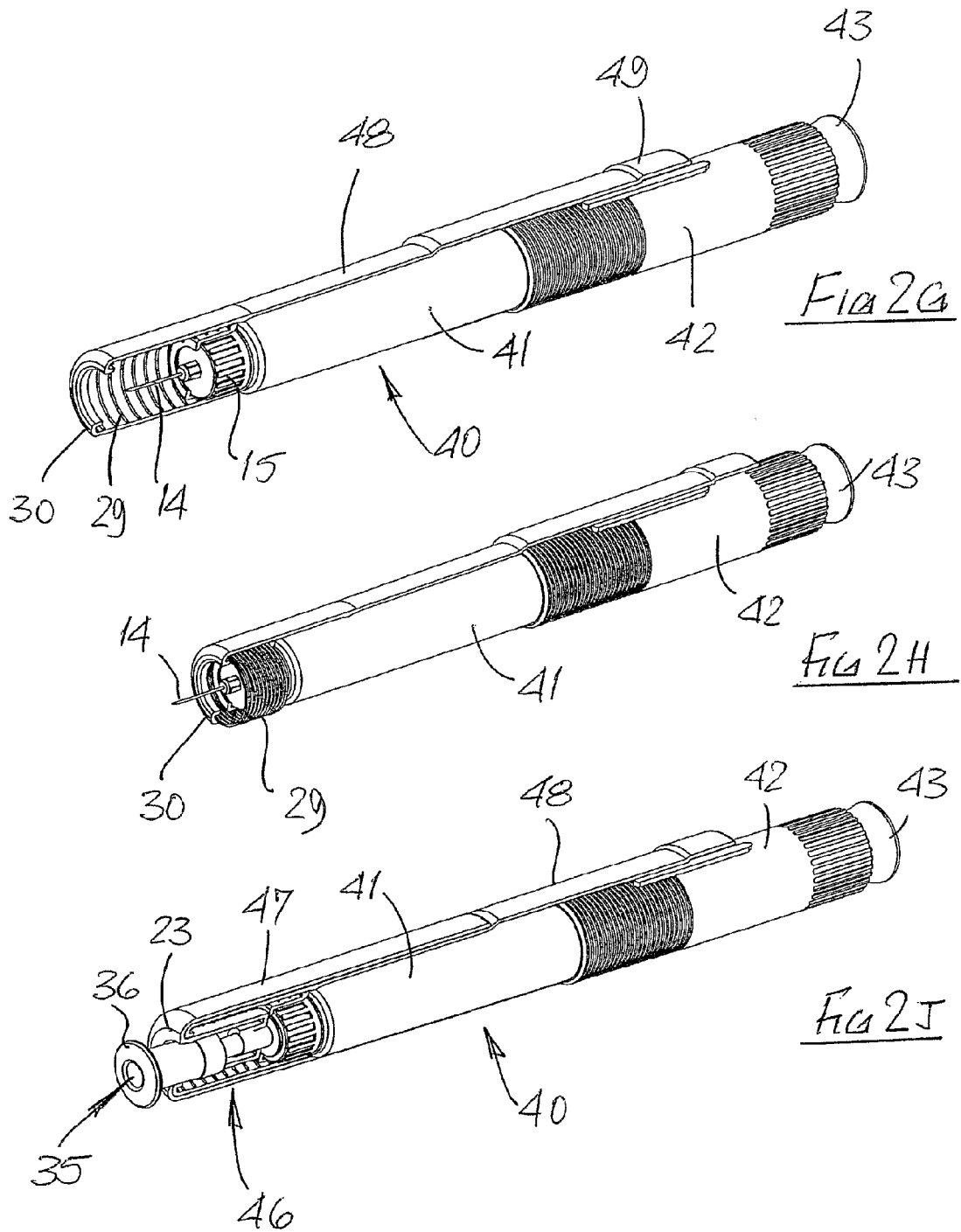

MEDICAL INJECTOR HANDLING DEVICE

CROSS-REFERENCE TO RELATED APPLICATIONS

This application is the U.S. national stage application of International Application PCT/GB2005/000487, filed 11 Feb. 2005, which international application was published on 1 Sep. 2005, as International Publication WO2005/079889 in the English language. The International Application claims priority of Great Britain Patent Application 0403335.3, filed 14 Feb. 2004, This invention relates to a handling device for use with a medical injector having a cylindrical body provided with a boss at the forward end thereof for supporting a forwardly projecting needle furnished with a protective sheath.

Throughout this specification, the terms forward and forwardly in relation to an injector refer to the end of the injector at which the needle is mounted and the direction towards that end. Conversely, the terms rearward and rearwardly refer to the end of the injector opposed to the forward end and the direction away from the forward end thereof.

A drug in the form of a liquid may be administered (other than orally) to a human or animal body by means of an injector having a hollow needle in conjunction with a source of the required liquid drug. For example, the hollow needle may be associated with a small-volume syringe holding the liquid drug, the needle being used to penetrate the body at an injection site, at which the drug is to be received.

In recent years, there has been a trend towards self-administered drug delivery systems. Following on from advances in drug technology, it is now possible to treat conditions which previously may not have been treatable or only treatable with difficulty, though with these advances it often is necessary to deliver the appropriate drugs at frequent and regular intervals. By facilitating self-administration, this eases the burden on the medical services, as well as on a patient who may perform the required drug delivery injection wherever that person happens to be, without needing to seek out the services of medically-qualified personnel.

A well-known and widely documented problem with needle-based drug delivery systems is the risk of so-called needle-stick injuries, where a person accidentally and inadvertently becomes injured by a needle. Before the needle has been used to perform an injection, this usually is of little consequence, but once the needle has been used, it may be a very much more serious matter. As such, there has been extensive research into and development of injection devices adapted to minimise the risk of needle-stick injuries.

Many people who are old or infirm might be suitable for treatment with self-administered injections, but are unable to perform the required safe operating procedures to minimise the risk of needle-stick injuries, either when preparing an injection device for administration of a drug, or subsequently when clearing-up after performing an injection and disposing of the used equipment. The present invention has been developed in an attempt to address these problems, particularly (but not exclusively) to facilitate the use of injection systems for the self-administration of drugs.

According to one aspect of this invention, there is provided a handling device for use with a medical injector having a cylindrical body provided with a boss at the forward end thereof supporting a forwardly-projecting needle furnished with a protective sheath, which device comprises:

a carrier having an outer cylindrical wall and co-axial therewith an inner tube which is a close sliding fit over the protective sheath of a needle;

a cylindrical sleeve slidably mounted within the outer cylindrical wall of the carrier, the rear end of the sleeve being adapted to receive the cylindrical body of the injector;

a bushing slidably located within the cylindrical sleeve, which bushing is retained within the sleeve and defines a bore for receiving the boss at the forward end of the injector body;

spring means urging the bushing towards the rear end of the sleeve; and a plug slidably mounted on the carrier and projectable from the forward end thereof, the forward end of the sheath of a received injector engaging the plug;

whereby in use the device may be fitted to the forward end of an injector by receiving the injector cylindrical body in the sleeve and the boss in the bore of the bushing, the sheath then coupling to the inner tube of the carrier and the forward end of the sheath engaging the plug and pushing the plug forwardly with respect to the carrier to project therefrom, and on subsequent withdrawal of the carrier from the injector, the bushing and sleeve remain on the injector and the sheath remains within the carrier with the plug projecting from the forward end thereof.

According to a further aspect of this invention, there is provided the combination of a handling device of this invention as described above, together with a medical injector having a cylindrical body provided with a boss at the forward end thereof for supporting a forwardly-projecting needle furnished with a protective a sheath, wherein the boss is receivable in the bore of the bushing, the sleeve is slidable rearwardly over the cylindrical body of the injector, and the sheath is connectable to the inner tube of the carrier.

According to yet another, and closely related, aspect of this invention, there is provided a method of using a handling device of this invention as described above, together with a medical injector having a cylindrical body provided with an externally-threaded boss at the forward end thereof for supporting a needle having an internally-threaded hub engageable with the threads of the boss and a needle sheath surrounding and protecting the needle. This method comprises the steps of:

threading the hub of a needle on to the boss of the injector;

pushing the carrier on to the forward end of the injector so that the injector body is slidably received in the cylindrical sleeve, the boss carrying the needle hub is received in the bore of the bushing, the sheath is coupled to the inner tube, and the sheath engages the plug and pushes the plug forwardly to project from the carrier;

pulling the carrier away from the cylindrical body of the injector with the sheath retained within the inner tube, the sleeve remaining on the injector body and the bushing remaining on the needle hub and boss, with the sleeve being urged forwardly by the spring to protect the needle;

and following the performance of an injection, during which the sleeve slides rearwardly over the injector body against the action of the spring to expose the needle as required:

pushing the carrier once more on to the forward end of the injector so receiving the sleeve into the carrier and refitting the sheath on to the needle;

rotating the carrier to unthread the needle hub from the boss and freeing the carrier from the injector body with the needle and sheath carried therewithin; and pressing the projecting plug back into the carrier, so driving the sheathed needle out of the handling device.

It will be appreciated that the handling device of this invention allows the handling of a hollow injection needle in a safe manner, so minimising the risk of a needle-stick injury, either before or after the performance of an injection procedure, by maximising the guarding of the needle tip. The device is fitted to an injector while the needle thereof still carries its protective sheath, and then on removing the carrier of the device from the injector, the needle is unsheathed. The cylindrical sleeve remains with the injector, surrounding and so shielding the needle from accidental contact which otherwise could damage the needle tip, leaving aside the risk of a needle-stick injury. On performing the injection, the cylindrical sleeve slides axially rearwardly with respect to the injector to expose the needle, the sleeve sliding back again under its spring loading to protect the needle, on withdrawing the needle from the injection site.

The fitting of the device to the injector as described above causes the plug, which is slidably mounted on the carrier, to be projected forwardly by the sheath. Then, on removing the carrier, the projecting plug indicates that the carrier contains the sheath and thus shows that the injector is ready to perform an injection.

The sheath may couple to the inner tube upon fully entering that tube, by being a light frictional fit within the tube. Typically, the sheath tapers slightly towards its free end so that it may easily enter a parallel bore defined by the inner tube, but then become gripped by the tube as the carrier is fully fitted to the injector. In an alternative arrangement, and depending upon the configuration of the sheath, a positive mechanical connection may be made between the sheath and the inner tube.

In a preferred aspect, following completion of the injection, the carrier may be refitted to the sleeve, so re-sheathing the needle. The entire device may then be removed from the injector in such a way that the sheathed needle remains within the device and so the sheathed needle is also removed from the injector, ready for disposal. For example, in the case of a needle having a hub which is threaded to the injector (as is usually the case for a self-administration injector), by turning the device in an unscrewing sense, the needle will be released from the injector with the device. Once removed from the injector, the carrier may be supported and on depressing the plug back thereinto, the sheathed needle will be driven out of the device, ready for disposal. For instance, the carrier containing the needle could be placed on a sharps container over the opening therein and the sheathed needle may then be discharged directly into the container. Alternatively, the device could be placed on a suitable surface such as a table-top and the plug depressed; the needle will quite safely be deposited on that surface for subsequent disposal, in view of the presence of the sheath on the needle.

In a preferred form of the invention, the carrier has an inner cylindrical wall connected at the forward end of the carrier to the outer cylindrical wall, the inner tube being connected to the rear end of the inner cylindrical wall. The cylindrical sleeve may thus be slidable within the annular space between the inner and outer cylindrical walls of the carrier, and the plug being slidably supported within the inner cylindrical wall.

Preferably, the plug is a sufficient light frictional fit within the cylindrical wall to restrain movement of the plug with respect to the carrier, at least under the influence of gravity, so that no false indication will be given that the needle is still sheathed when in fact the sheath has been removed and is located within the carrier. Further, the plug may have a highly visible colour to ensure it gives an adequate warning of the fact a needle has been unsheathed.

The rear end of the sleeve is advantageously internally profiled to permit the bushing to be pushed into the sleeve, whereafter the bushing is retained within the sleeve. For example, radially inwardly-directed nibs or an annular internal rib may be provided on the sleeve and with which the bushing is engageable.

Many injectors intended for the self-administration of drugs are in the form of a so-called pen injector, having an elongate cylindrical outer body with a boss for a needle hub at a forward end of the body and a mechanism at the rear end of the body, permitting pre-selection of a required dose and then operable to dispense that dose. A handling device of this invention for use with such a pen injector may have a cylindrical sleeve of a sufficient length to enclose the greater part of the length of the pen injector body, when the carrier is fitted to the injector, but still permitting access to the mechanism at the rear end of the injector body. Then, on performing the injection, the sleeve may be gripped in the fist of a user, in the same way as a user would grip the body of the injector if being used without the handling device of this invention. Once held in this way, the injector may be used in much the same way as would be a pen injector.

By having an elongate sleeve as just described, there follows the advantage that the forward end of the sleeve may be offered to the injection site at the required angle (and usually substantially perpendicularly), whereafter the pre-set mechanism at the rear end of the injector body may be depressed by a finger or thumb of the user. The initial pressure on that mechanism serves to move the entire injector forwardly within the sleeve, against the action of the spring acting between the bushing and the sleeve, so achieving needle penetration at the injection site. Continued pressure on the mechanism then dispenses the drug through the needle into the injection site. In this way, an injection may be performed in one simple and continuous action, rather than the user having to perform a first step of inserting the needle into the injection site and then a second and quite separate step of actuating the dispensing mechanism. Further, the needle remains shielded from the direct view of a patient, so assisting with the well-recognised aversion to needles suffered by many people.

By way of example only, two specific embodiments of handling device for use with a medical injector will now be described in detail, reference being made to the accompanying drawings, in which:

FIGS. 1A to 1G show a first embodiment of handling device of this invention in association with an injector, the handling device having a relatively short outer sleeve, wherein FIGS. 1A to 1G are axial sections through the handling device and a part of the injector showing the successive steps of the use of the injector and handling device to perform an injection;

FIG. 1G shows the first embodiment of handling device at the end of an injection procedure with the re-sheathed needle ejected from the device; and FIGS. 2A to 2H and 2J show a handling device in association with a pen injector intended for the self-administration of a drug, wherein FIG. 2A shows the pen injector with the handling device fitted thereto, but before a disposable needle has been mounted on the injector, FIG. 2B is a partial sectional view of the assembly of FIG. 2A, and FIGS. 2C to 2H and 2J show successive steps of the use of the injector and handling device to perform an injection.

Note: the capital letter I is not used in the numbering of the Figures, to avoid confusion with the numeral 1.

Referring initially to FIGS. 1A to 1F, there is shown a first embodiment of handling device 10 for use with an injector 11. The injector comprises a cylindrical body 12 having an externally-threaded boss 13 at its forward end adapted for the connection thereto of a needle 14 having an internally screw-threaded hub 15. A plunger (not shown) and including a piston (also not shown) at its forward end is slidably mounted within the body 12, to permit filling of the injector with a liquid medicament (drug) and then the dispensing of that medicament through an attached needle. Alternatively, a vial of the medicament and having an integral piston may be located within the body 12, the vial having a pierceable membrane at its forward end for penetration by the rear end of an attached needle.

As shown in FIGS. 1A and 1B, the needle is carried in a stub 16 forming a part of the hub 15, and a sheath 17 is fitted over the needle, that sheath being engaged with the stub 16. The sheath is formed of a substantially rigid plastics material and has a rear flange 18 engaged with the needle hub 15. As such, the sheath will protect the needle against accidental contact during fitting of the needle to the injector 11 by threading the hub 15 on to the boss 13, the sheath being restrained against lateral movement with respect to the needle by virtue of the flange 18.

The handling device 10 has a carrier 20 defining an outer cylindrical wall 21 and an inner cylindrical wall 22 connected to the outer cylindrical wall at the forward end of the carrier by a further wall 23. Slidably mounted within the carrier, adjacent the outer cylindrical wall, is a cylindrical sleeve 24 internally profiled to permit the cylindrical body 12 of the injector to slide freely therewithin. The bore of the cylindrical sleeve 24 slidably carries a bushing 25 having an outer wall 26 which runs on the internal surface of the cylindrical sleeve, and an inner wall 27 adapted to receive the hub of a needle fitted to the injector The rear end portion of the cylindrical sleeve 24 has an internal inwardly-projecting annular rib 28 over which the bushing may be bumped when fitting the bushing to the sleeve, but then serves to retain the bushing within the sleeve 24. A helical compression spring 29 is disposed within the sleeve 24 and acts between a forward flange 30 of the sleeve and the bushing 25, to urge the bushing towards the rear of the sleeve.

The rear end of the inner cylindrical wall 22 has an internally directed flange 32 supporting an inner tube 33 projecting forwardly from that flange. The bore of the tube is dimensioned so as to be able to receive the sheath 17 protecting the needle, but to be a friction fit over the rear part of that sheath, thereby to grip the sheath when fitted thereto.

The handling device further includes a plug 35 slidably mounted within the inner cylindrical wall 22 of the carrier 20. The rear end of the plug is provided with a shoulder engageable with an internal step formed in the bore of the inner cylindrical wall 22, thereby to limit outward movement of the plug, from the carrier. The plug 35 has an enlarged head 36, which, in its normal position shown in FIGS. 1A and 1B, rests against the further wall 23 of the carrier. When in this position, a conical bore formed in the rear end of the plug locates around the forward end of the inner tube 33, also being a part of the carrier 20. An internal wall 37 separates the conical bore from the forward part of the plug. The plug 35 is a light frictional fit within the inner cylindrical wall 22 so that it will move with respect thereto only when positively pushed by an external force.

FIGS. 1A and 1B show the handling device 10 ready for use with the injector 12, to which a needle has already been attached by threading its hub 15 to the boss 13 of the injector, the sheath 17 remaining on the needle during this action to protect a user from accidental contact with the needle and also possible injury. In this condition, the injector has been pre-loaded with the medicament to be injected.

To commence an injection procedure, the handling device 10 is fitted to the forward end of the injector, simply by being pushed thereon. The cylindrical body 12 of the injector locates within the cylindrical sleeve 24 and the bushing 25 is pushed on to the outer surface of the needle hub 15, by the interaction of the rear end of the cylindrical wall 22 of the carrier, with the forward end of the bushing 25. Further, the inner tube 23 is driven on to the sheath 17 protecting the needle. In view of the length of the sheath, part-way through fitting the handling device to the injector, the front end of the sheath contacts the internal wall 37 of the plug 35. In view of rigid character of the sheath, completing the fitting of the handling device to the injector drives the plug forwardly, partially out of the carrier as shown in FIG. 1C.

Following the complete fitting of the handling device on the injector, the carrier 20 is gripped and pulled away from the injector, as shown in FIG. 1D. This action removes the sheath 17 from the needle but leaves the cylindrical sleeve 24 on the injector, held in place by the bushing 25 engaged with the outer surface of the needle hub 15. The spring 29 maintains the sleeve 24 in its fully forward position, with the internal rib 28 thereof engaged with the rear end of the bushing 25. The injector is now ready to perform an injection.

Also as shown in FIG. 1D, the presence of the plug projecting from the carrier 20 indicates to a user that the needle is unsheathed, and so is ready for use. Further, as the carrier is restrained for generally axial movement by the sleeve 24 located on the injector, the sheath is removed axially with respect to the needle and so will not contact that needle. In this way, damage to the sharp tip of the needle is avoided.

An injection is performed by presenting the forward end of the cylindrical sleeve 22 to an injection site, typically with the injector generally perpendicular to the skin. The injector is then pushed forwardly to achieve penetration by the needle, the sleeve 24 retreating by sliding along the injector body against the action of spring 29, as shown in FIG. 1E. The plunger of the injector may then be depressed to dispense the required dose of the medicament, through the needle 14 into the patient at the injection site. Both actions may be completed essentially continuously, by gripping the sleeve 24 and pressing the plunger, firstly to achieve needle penetration and then to complete the injection.

Following completion of the injection, the injector is withdrawn from the injection site, the sleeve 24 moving forwardly during this under the action of the spring 29 until the injector condition shown in FIG. 1D is achieved once more. Then, the carrier 20 is picked up and is again pressed onto the forward end of the injector, so re-sheathing the needle. This is essentially the same condition as is shown in FIG. 1C, except that an injection has been performed. Again, the carrier is moved axially by virtue of the presence of the cylindrical sleeve 24 on the injector and so re-sheathing of the needle may be achieved without risk of the needle engaging the internal wall of the sheath or possibly even penetrating the wall of the sheath.

In the position of FIG. 1F, the sheath is still gripped by the inner tube 23 and the outer surface of the needle hub 15 remains engaged with the bore of the bushing 25, gripped thereby. The handling device 10 is removed from the injector by rotating the carrier 20 in an unscrewing sense (that is, counter-clockwise when viewed from the forward end of the injector) so unthreading the needle hub 15 from the threaded boss 13 of the injector. The needle hub eventually comes free of the injector so that the entire handling device together with the needle located therewithin may be moved away from the injector (FIG. 1F).

The procedure is completed by pressing the plug 35 back into the carrier 20, so ejecting the sheathed needle therefrom (FIG. 1G). To perform this, the carrier could simply be held in one hand and the plug pushed in with a finger of the other hand, the carrier being held over a suitable receptacle for used needles such as a sharps container. Alternatively, the carrier could be stood on a suitable surface such as a desktop with the plug uppermost, whereafter the plug is pressed downwardly so freeing the needle from the carrier. As the needle is sheathed, there is no more risk attaching to this than when a fresh needle is mounted on the forward end of the injector.

FIGS. 2A to 2J shown a second embodiment of this invention, expressly adapted for use with a pen type of injector intended for the self-administration of medicaments. Insofar as there are components common with those described above with reference to the first embodiment, those components will be given like reference characters and will not be described again here.

The pen injector 40 is essentially conventional and so will not be described in detail. Briefly, the injector includes a cylindrical body 41 within which may be mounted a vial of the medicament to be self-administered, the forward end of that body having a threaded boss 13 to which may be secured a needle 14 having an internally-threaded hub 15. The rear end of the injector includes a mechanism 42 allowing the pre-selection of a dose of medicament and then, on depressing a plunger 43, the pre-set dose is dispensed out of an attached needle 14. Such mechanisms are well-known and form no part of the present invention. A removable cap 44 is provided for the mechanism 42.

The handling device 46 of this second embodiment is functionally identical to that of the first embodiment but differs in that it is provided with a carrier 47 and a cylindrical sleeve 48 both having significantly greater axial lengths than the corresponding components of the first embodiment, such that the greater part of the cylindrical body 41 of the pen injector 40 is contained within the sleeve 48, when the handling device is fitted to the injector. FIGS. 2A and 2B show the handling device 46 fitted to the injector with the cap 44 in place, this being the normal storage condition for the injector. The rear end portion of the cylindrical sleeve is provided with a skirt 49 with which the forward end of the cap 44 engages, so wholly containing the pen injector. No needle is fitted to the injector and the plug 35 is in its rearmost position, within the handling device.

To prepare the injector for the self-administration of an injection, the cap 44 is removed (FIG. 2C) and then the handling device 46 is pulled away from the injector (FIG. 2D). An entirely conventional self-injection sheathed needle assembly 50 is then threaded on to the boss 13 at the forward end of the injector body 41 (FIG. 2E), whereafter the handling device 46 is pushed on to the injector body (FIG. 2F), so causing the plug 35 to project forwardly from the handling device, as has been described above with reference to FIG. 1C.

With the bushing 25 now engaged with the needle hub 15, the sleeve 48 is held to the injector body; on pulling the carrier 47 axially away therefrom (FIG. 2G), the sleeve 48 remains on the injector, in its fully forward position urged by spring 29. Following this, the required dose is pre-set on the mechanism 42 at the rear end of the injector, so that the injector is ready for performing an injection.

The injection, is performed by grasping the sleeve 48 in the fist of a user, typically with the thumb over the plunger 43, such that the plunger may be depressed thereby The forward end of the sleeve 48 is presented to the injection site, and then the thumb is used to depress the plunger 43 with respect to the sleeve 48, which is held stationary by the operator. This initially causes the injector 40 to move forwardly within the sleeve 48 against the action of spring 29, so achieving needle penetration at the injection site. By maintaining the pressure on the plunger, when the injector has moved fully forwardly (FIG. 2F) the dispensing mechanism of the plunger is activated, so driving the required dose out of the needle 14, into the injection site. Thus, only one simple action is required by the user, to achieve both needle penetration and dispensing of the medicament, which may be contrasted with the conventional procedure using a pen injector, where the two actions are performed quite separately.

On withdrawing the injector from the injection site, the injector 40 moves rearwardly with respect to the sleeve 48 (FIG. 2G) and then the carrier 47 may once more be fitted to the sleeve (FIG. 2H). The overall procedure may now be completed in one of two ways. In the first, the carrier 47 may be gripped and the plunger 35 pushed inwardly, so ejecting from the holding device the injector with the sheathed needle attached, whereafter the needle may be unscrewed from the injector and disposed of, as is currently performed with pen injectors. In the alternative, the carrier may be unscrewed in the same manner as has been described above with reference to the first embodiment, such that the handling device 46 comes away from the injector with the sheathed needle still within that device. Thereafter, the carrier may be gripped and the plug pushed inwardly, to eject the sheathed needle from the handling device.

With both embodiments of this invention, there are the advantages of:

Greatly enhanced operator safety, with no risk of accidental injury unlike the use of a conventional injector, were an attempt made to re-sheath the needle following the performance of an injection.

Safety for all people in any way involved in the procedure, since the needle remains sheathed whenever detached from the injector.

An injection may be performed with a single continuous action, rather than having separately to perform a first step of achieving needle penetration and then a second step of dispensing of the medicament.

The sleeve makes it easier to achieve true axial penetration for the needle, so reducing the risk of pain to a patient.

The needle is unsheathed without there being risk of the sheath contacting, and so damaging, the sharp tip of the needle.

The needle itself is at all times concealed from the patient, either by the sheath or by the cylindrical sleeve once the handling device has been fitted to the injector, so reducing distress to a patient suffering needle aversion.

The invention claimed is:

1. A handling device for use with a medical injector having a cylindrical body provided with a boss at the forward end thereof supporting a forwardly-projecting needle furnished with a substantially rigid protective sheath, which device comprises:

a carrier having an outer cylindrical wall and co-axial therewith an inner tube which is a close sliding fit over the protective sheath of the needle;

a cylindrical sleeve slidably mounted within the outer cylindrical wall of the carrier, a rear end of the sleeve being adapted to receive the cylindrical body of the injector;

a bushing slidably located within the cylindrical sleeve, which bushing is retained within the sleeve and defines a bore for receiving the boss at the forward end of the injector body;

spring means urging the bushing towards the rear end of the sleeve; and a plug mounted on the carrier for sliding movement between an inactive position where the plug is located substantially wholly within the carrier and an indicating position where the plug projects from the carrier, the plug having a wall disposed for engagement by a forward end of the protective sheath of the needle to effect said sliding movement;

whereby in use the device is fitted to the forward end of the injector by receiving the injector cylindrical body in the sleeve and said boss of the injector in the bore of the bushing, the protective sheath then coupling to the inner tube of the carrier and the forward end of the sheath engaging said wall of the plug so pushing the plug forwardly with respect to the carrier to project therefrom, and on subsequent withdrawal of the carrier from the injector, the bushing and sleeve remain on the injector and the sheath remains within the carrier with the plug projecting from the forward end thereof in its indicating position.

2. A handling device as claimed in claim 1, wherein the carrier has an inner cylindrical wall connected at the forward end of the carrier to the outer cylindrical wall, the inner tube being connected to the rear end of the inner cylindrical wall.

3. A handling device as claimed in claim 2, wherein the cylindrical sleeve is slidable within the annular space between the inner and outer cylindrical walls of the carrier.

4. A handling device as claimed in claim 2, wherein the plug is slidably supported within the inner cylindrical wall of the carrier.

5. A handling device as claimed in claim 4, wherein the plug is a sufficient light frictional fit within said inner cylindrical wall of the carrier to restrain movement of the plug with respect to the carrier under the influence of gravity.

6. A handling device as claimed in claim 4, wherein the length of the plug is such that the plug is substantially wholly accommodated within the carrier prior to use of the device with the injector.

7. A handling device as claimed in claim 4, wherein the plug and the forward end of the inner cylindrical wall of the carrier co-operate to limit forward movement of the plug, out of the carrier.

8. A handling device as claimed in claim 1, wherein the plug has an enlarged head at its forward end which lies externally of the carrier.

9. A handling device as claimed in claim 1, wherein the sleeve has a rear end which is internally profiled to permit the bushing to be pushed into said rear end of the sleeve thereafter to retain the bushing within the sleeve.

10. A handling device as claimed in claim 9, wherein the rear end of the sleeve has an internal profile which includes one or more radially-inwardly directed nibs with which the bushing is engageable.

11. A handling device as claimed in claim 1, wherein the bushing includes an in-turned lip at the forward end thereof, which lip is engageable by the forward end of the injector boss to define an engaged relative position of the injector and the bushing.

12. A handling device as claimed in claim 11, wherein the carrier has an inner cylindrical wall connected at the forward end of the carrier to the outer cylindrical wall, the inner tube being connected to the rear end of the inner cylindrical wall, and said lip of the bushing engages the rear end of the inner tube when the cylindrical sleeve is fully within the outer cylindrical wall of the carrier.

13. A handling device as claimed in claim 1, wherein the plug has a rearwardly-facing socket within which the forward end of the protective sheath of the injector is receivable.

14. A handling device as claimed in claim 1, wherein the spring means comprises a helical compression spring located within the sleeve and acting between the forward end of the sleeve and the bushing.

15. A handling device as claimed in claim 1, wherein the boss at the forward end of the cylindrical body is externally screw-threaded, for use with the needle having a hub with an internally-threaded socket co-operable with the threads of the boss.

16. A handling device as claimed in claim 1, wherein the carrier has an inner cylindrical wall connected at the forward end of the carrier to the outer cylindrical wall, the inner tube being connected to the rear end of the inner cylindrical wall, and the rear end of the plug locates in an annular space between the inner cylindrical wall of the carrier and the inner tube, when the plug is fully within the carrier.

17. A handling device as claimed in claim 1, wherein the plug is of a contrasting color to that of the carrier.

18. A handling device as claimed in claim 1, wherein the sleeve defines an elongate internal cavity of a sufficient length to accommodate the body of the medical injector having a plunger and intended for self administration, leaving only the plunger of the injector accessible.

19. The combination of a handling device as claimed in claim 1 and a medical injector having a cylindrical body provided with a boss at the forward end thereof for supporting a forwardly-projecting needle furnished with a protective sheath, wherein the boss is receivable in the bore of the bushing, the sleeve is slidable rearwardly over the cylindrical body of the injector, and the sheath is connectable to the inner tube of the carrier.

20. A method of using a handling device as claimed in claim 1 with a medical injector having a cylindrical body provided with an externally threaded boss at the forward end thereof for supporting a needle having an internally threaded hub engageable with the threads of the boss and a substantially rigid needle sheath surrounding and protecting the needle, comprising the steps of:

threading the hub of the needle on to the boss of the injector;

pushing the carrier on to the forward end of the injector so that the injector body is slidably received in the cylindrical sleeve, the boss carrying the needle hub is received in the bore of the bushing, the sheath is coupled to the inner tube, and the sheath engages said wall in the plug to push the plug forwardly to said indicating position, projecting from the carrier;

pulling the carrier away from the cylindrical body of the injector with the sheath retained within the inner tube, the sleeve remaining on the injector body and the bushing remaining on the needle hub and boss, with the sleeve being urged forwardly by the spring means to protect the needle;

and following the performance of an injection, during which the sleeve slides rearwardly over the injector body against the action of the spring means to expose the needle as required:

pushing the carrier once more on to the forward end of the injector so receiving the sleeve into the carrier and refitting the protective sheath on to the needle;

rotating the carrier to unthread the needle hub from the boss and freeing the carrier from the injector body with the needle and sheath carried therewithin; and pressing the projecting plug back into the carrier, so driving the sheathed needle out of the handling device.

* * * * *